(12) United States Patent
Kacira et al.

(10) Patent No.: US 11,261,474 B2
(45) Date of Patent: Mar. 1, 2022

(54) OPTICAL DEVICE FOR IN-LINE AND REAL-TIME MONITORING OF MICROORGANISMS

(71) Applicant: ARIZONA BOARD OF REGENTS ON BEHALF OF THE UNIVERSITY OF ARIZONA, Tucson, AZ (US)

(72) Inventors: Murat Kacira, Tucson, AZ (US); Fei Jia, Tucson, AZ (US); Kimberly L. Ogden, Tucson, AZ (US); Gregory E. Ogden, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 104 days.

(21) Appl. No.: 15/739,467

(22) PCT Filed: Jun. 29, 2016

(86) PCT No.: PCT/US2016/040147
§ 371 (c)(1),
(2) Date: Dec. 22, 2017

(87) PCT Pub. No.: WO2017/004236
PCT Pub. Date: Jan. 5, 2017

(65) Prior Publication Data
US 2018/0187234 A1 Jul. 5, 2018

Related U.S. Application Data

(60) Provisional application No. 62/186,047, filed on Jun. 29, 2015.

(51) Int. Cl.
*C12Q 1/02* (2006.01)
*C12M 1/00* (2006.01)
(Continued)

(52) U.S. Cl.
CPC ............... *C12Q 1/02* (2013.01); *C12M 21/02* (2013.01); *C12M 23/04* (2013.01); *C12M 23/18* (2013.01);
(Continued)

(58) Field of Classification Search
None
See application file for complete search history.

(56) References Cited

U.S. PATENT DOCUMENTS 4,444,882 A * 4/1984 Shimizu ................. C12M 41/36
435/29
5,407,638 A * 4/1995 Wang ...................... G01N 21/05
250/576

(Continued)

OTHER PUBLICATIONS

Barclay, W.R.; Meager, K.M.; Abril, J.R. Heterotrophic production of long chain omega-3 fatty acids utilizing algae and algae-like microorganisms. J Appl Phycol. 1994, 6(2), 123-129.
(Continued)

*Primary Examiner* — Kara E. Geisel
*Assistant Examiner* — Jarreas C Underwood
(74) *Attorney, Agent, or Firm* — Nguyen Tarbet LLC

(57) ABSTRACT

A multi-wavelength laser diode based optical sensor system capable of monitoring the dynamics and physiological changes of a microorganism culture in real-time. The microorganism culture from a microorganism production chamber is pumped to a flow chamber. Laser diodes emit light at certain wavelengths through the flow chamber, which is sensed by photodiodes. A laser control circuitry is operatively connected to the laser diodes and a signal conditioning circuitry is operatively connected to the photodiodes. A microprocessor reads and records voltage signals corresponding to the wavelengths. A data acquisition system converts said voltage signals into measurements of biologi-
(Continued)

cal parameters, which are displayed on a graphical user interface and allow a user to monitor the measurements in real time.

13 Claims, 7 Drawing Sheets

(51) Int. Cl.
| | |
|---|---|
| C12M 1/12 | (2006.01) |
| C12M 1/34 | (2006.01) |
| G01N 1/00 | (2006.01) |
| G01J 1/00 | (2006.01) |

(52) U.S. Cl.
CPC ............ *C12M 29/08* (2013.01); *C12M 41/06* (2013.01); *C12M 41/36* (2013.01)

(56) References Cited

U.S. PATENT DOCUMENTS

| | | | | | |
|---|---|---|---|---|---|
| 5,553,616 | A | * | 9/1996 | Ham | A61B 5/14558 600/316 |
| 7,413,891 | B2 | * | 8/2008 | Bashir | B01L 3/502753 137/822 |
| 7,709,821 | B2 | * | 5/2010 | Casstevens | G01J 3/0218 250/573 |
| 8,244,477 | B1 | * | 8/2012 | Embaye | G01N 21/59 702/19 |
| 8,269,952 | B2 | | 9/2012 | Ueno | |
| 9,678,244 | B2 | * | 6/2017 | Shen | E21B 49/081 |
| 2002/0053640 | A1 | * | 5/2002 | Kester | G01N 21/359 250/339.09 |
| 2003/0054558 | A1 | | 3/2003 | Kurabayashi et al. | |
| 2004/0072278 | A1 | * | 4/2004 | Chou | B01L 3/502761 435/29 |
| 2008/0221711 | A1 | * | 9/2008 | Trainer | G01N 15/0205 700/54 |
| 2009/0170149 | A1 | * | 7/2009 | Viator | G01N 21/1702 435/29 |
| 2011/0054864 | A1 | * | 3/2011 | Lundstedt | G01N 21/274 703/2 |
| 2011/0066382 | A1 | * | 3/2011 | Adams | G01N 21/53 702/19 |
| 2011/0176127 | A1 | * | 7/2011 | Kanda | G01N 15/1429 356/72 |
| 2011/0222062 | A1 | * | 9/2011 | Martini | G01J 3/28 356/417 |
| 2014/0287449 | A1 | * | 9/2014 | Bonyuet | C12Q 1/02 435/29 |
| 2015/0107993 | A1 | * | 4/2015 | Izquierdo | G01N 33/1866 204/403.01 |
| 2018/0011016 | A1 | * | 1/2018 | Swalwell | G01N 15/1459 |

OTHER PUBLICATIONS

Briassoulis, D.; Panagakis, P.; Chionidis, M.; et al. An experimental helical-tubular photobioreactor for continuous production of *Nannochloropsis* sp. Bioresour Technol. 2010, 101(17), 6768-6777.

Chen, Y.; Vaidyanathan, S. A simple, reproducible and sensitive spectrophotometric method to estimate microalgal lipids. Anal Chim Acta. 2012, 724(0), 67-72.

Chisti, Y. Biodiesel from microalgae. Biotechnol Adv. 2007, 25(3), 294-306.

Collos, Y.; Mornet, F.; Sciandra, A.; Waser, N.; Larson, A.; Harrison, P.J. An optical method for the rapid measurement of micromolar concentrations of nitrate in marine phytoplankton cultures. J Appl Phycol. 1999, 11(2), 179-184.

Harun, R.; Singh, M.; Forde, G.M.; Danquah, M.K. Bioprocess engineering of microalgae to produce a variety of consumer products. Renew Sust Energ Rev. 2010, 14(3), 1037-1047.

Held P. Monitoring of algal growth using their intrinsic properties. Available online: http://www.biotek.com/resources/articles/monitoring-of-algal-growth-using-intrinsic-properties.html (Accessed on Jul. 11, 2011).

Jones, S.B.; Zhu, Y.; Anderson, D.B.; Hallen, R.T.; Elliott, D.C.; Schmidt, A.J.; et al. Process Design and Economics for the Conversion of Algal Biomass to Hydrocarbons: Whole Algae Hydrothermal Liquefaction and Upgrading. PNNL-23227, Pacific Northwest National Laboratory, Richland, WA. 2014.

Lee, S.; Yoon, B.; Oh, H. Rapid method for the determination of lipid from the green alga botryococcus braunii. Biotechnol Tech. 1998, 12(7), 553-556.

López, M.C.G.; Sanchez, E.D.R.; López, J.L.C.; et al. Comparative analysis of the outdoor culture of haematococcus pluvialis in tubular and bubble column photobioreactors. J Biotechnol. 2006, 123(3), 329-342.

Marxen, K.; Vanselow, K.; Lippemeier, S.; Hintze, R.; Ruser, A.; Hansen, U. A photobioreactor system for computer controlled cultivation of microalgae. J Appl Phycol. 2005, 17(6), 535-549.

Mata, T.M.; Martins, A.A.; Caetano, N.S. Microalgae for biodiesel production and other applications: A review. Renew Sust Energ Rev. 2010, 14(1), 217-232.

Meireles, L.A.; Azevedo, J.L.; Cunha, J.P.; Malcata, F.X. On-line determination of biomass in a microalga bioreactor using a novel computerized flow injection analysis system. Biotechnol Prog. 2002, 18(6), 1387-1391.

Nedbal, L.; Trtílek, M.; Červený, J.; Komárek, O.; Pakrasi, H.B. A photobioreactor system for precision cultivation of photoautotrophic microorganisms and for high-content analysis of suspension dynamics. Biotechnol Bioeng. 2008, 100(5), 902-910.

Ogbonna, J.C.; Tanaka, H. Night biomass loss and changes in biochemical composition of cells during light/dark cyclic culture of Chlorella pyrenoidosa. Journal of Fermentation and Bioengineering. 1996, 82 (6), 558-564.

Perez-Garcia, O.; Escalante, F.M.E.; De-Bashan, L.E.; Bashan, Y. Heterotrophic cultures of microalgae: Metabolism and potential products. Water Res. 2011, 45(1), 11-36.

Radakovits, R.; Jinkerson, R.E.; Darzins, A.; Posewitz, M.C. Genetic engineering of algae for enhanced biofuel production. Eukaryot Cell. 2010, 9(4), 486-501.

Richmond, A.; Zhang, C.W. Optimization of a flat plate glass reactor for mass production of *Nannochloropsis* sp. outdoors. J Biotechnol. 2001, 85(3), 259-269.

Sandnes, J.M.; Ringstad, T.; Wenner, D.; Heyerdahl, P.H.; Källqvist, T.; Gislerød, H.R. Real-time monitoring and automatic density control of large-scale microalgal cultures using near infrared (NIR) optical density sensors. J Biotechnol. 2006, 122(2), 209-215.

Solovchenko, A.; Khozin-Goldberg, L; Recht, L.; Boussiba, S. Stress-induced changes in optical properties, pigment and fatty acid content of *Nannochloropsis* sp.: Implications for non-destructive assay of total fatty acids. Mar Biotechnol. 2011, 13(3), 527-535.

Su, C.; Fu, C.; Chang, Y.; et al. Simultaneous estimation of chlorophyll a and lipid contents in microalgae by three-color analysis. Biotechnol Bioeng. 2008, 99(4), 1034-1039.

Wiltshire, K.; Boersma, M.; Moller, A.; Buhtz, H. Extraction of pigments and fatty acids from the green alga scenedesmus obliquus (chlorophyceae). Aquat Ecol. 2000, 34(2), 119-126.

Yao, Y.; Thommasson, J.A.; Ge, Y.; Sui, R. Improvement of an optical density sensor for algae pond monitoring and process control. 2012 ASABE Paper No. 12-1338431, St. Joseph, Mich.: ASABE.

Zhu, C.J.; Lee, Y.K. Determination of biomass dry weight of marine microalgae. J Appl Phycol. 1997, 9(2), 189-194.

6131 and 6132 blue-green algae sensors (6-series). Available online: http://www.ysi.com/accessoriesdetail.php?6131-and-6132-Blue-Green-Algae-Sensors-6-Series-91. (Accessed on Jul. 12, 2013).

AlgaeTorch—chlorophyll and cyanobacteria measurement. Available online: http://www.bbe-moldaenke.de/chlorophyll/algaetorch/ (Accessed on Jul. 12, 2013).

Blue-green algae by sensor turner designs. Available online: http://www.hachhydromet.com/web/ott_hach.nsf/id/pa_blue-green_algae_by_turner_designs.html (Accessed on Feb. 10, 2012).

(56) References Cited

OTHER PUBLICATIONS

Unique design of EXO total algae sensor combines chlorophyll and blue-green algae for greater accuracy. Available online: http://www.exowater.com/blognow/blogDetail.php?Unique-Design-of-EXO-Total-Algae-Sensor-Combines-Chlorophyll-and-Blue-green-Algae-for-Greater-Accuracy-3 (Accessed on Jul. 12, 2013).

* cited by examiner

OPTICAL DEVICE FOR IN-LINE AND REAL-TIME MONITORING OF MICROORGANISMS

CROSS REFERENCE

This application claims priority to U.S. Provisional Patent Application No. 62/186,047, filed Jun. 29, 2015, the specification(s) of which is incorporated herein in their entirety by reference.

GOVERNMENT SUPPORT

This invention was made with government support under Grant No. DE-EE0006269 awarded by DOE. The government has certain rights in the invention.

FIELD OF THE INVENTION

The present invention relates to optical sensor systems, in particular, a multi-wavelength laser and photo diode based optical sensor unit for in-line monitoring of aqueous suspension system dynamics in real-time. Alternative embodiments of the invention may be used for in-line analysis and/or control of said system dynamics in real-time when integrated with a controller.

BACKGROUND OF THE INVENTION

Microalgae have been successfully used as feedstock for the production of pharmaceutical products, nutritional supplements and chemicals. Certain species of microalgae are candidates for the production of biofuels due to their high productivity and high oil content. Producing sufficient amounts of biomass with controlled quality is the premise for production of microalgae derived products. Optimizing resource inputs and maintaining high productivity are the key components to control the quantity, quality and cost of the algae production. Real-time monitoring provides the platform to acquire the environmental and physiological dynamics of a microalgae culture system. For large scale microalgae production systems, effective decision making and overall production system management in terms of optimal resource use, harvesting and culture condition optimization (media composition, lighting, temperature, pH, dissolved oxygen levels etc.) is crucial in order to achieve maximum profit and to prevent or reduce economic losses in case of contamination.

Measurements of biological variables, including cell concentration, cell size, cell morphology, population composition (i.e. concerns with contamination), pigments and lipid content, are especially desirable because they are the direct indicators of the dynamics of a microalgae culture system. Standard methods developed for measurements of these variables are either too laborious or destructive to be employed for real-time monitoring and control purposes. Spectrophotometry has been widely used to estimate these biological variables by measuring the absorbance, turbidity or fluorescence of the culture suspension. As a non-destructive and rapid analytical method, spectrophotometry became a preferable candidate for real-time monitoring of microalgae culture systems. There are commercialized sensors to monitor microalgae concentration. However, most are designed to monitor microalgae concentration at an environmental level which is much lower than the cell concentration in microalgae production applications. Furthermore, these sensors are too expensive for low added value product applications. Therefore, they are not practical to integrate into outdoor raceway or photobioreactor (PBR) based algae production systems.

There have been only a few studies on development and evaluation of optical sensors for microalgae monitoring and control applications. For instance, Sandes et al. [*J Biotechnol.* 2006, 122(2), 209-215] focused on measuring the light intensity transmitted through a transparent production tube with a 10 mm light path length containing a microalgae suspension using an LED (880 nm) and photodiode pair mounted on opposite sides of the tube. As another example, Briassoulis et al. [*Bioresour Technol.* 2010, 101(17), 6768-6777] developed an automated flow-through density sensor and harvesting system for *Nannochloropsis* sp. The LEDs paired with photosensors integrated into the system were used to measure the light transmittance of cell culture at 470, 518, 630 and 940 nm. The system used a neural network to estimate biomass concentration by associating the voltage readings from each photosensor with the cell concentration measured by cell count. The sensor reported has a maximum error at 9% within an interval of 5 to $145 \times 10^6$ cells $mL^{-1}$, which is a relatively high error rating.

Nedbal et al. [*Biotechnol Bioeng.* 2008, 100(5), 902-910] described the monitoring of chlorophyll concentration and cell density of a cyanobacterial suspension by a flat-cuvette photobioreactor with a built-in fluorometer and densitometer. Blue LEDs (455 nm) and orange LEDs (627 nm) were used for excitation of blue absorption and phycobilins, respectively. The optical density of the suspension was measured at 680 nm and 735 nm. Cell count and chlorophyll concentration were linearly proportional to optical density (OD) 680 in the range 0.1-1.2 and to OD 735 in the range 0.02-0.4. However, these values of OD or cell density are typically exceeded in microalgae production systems. Furthermore, the sensor unit was designed for a specific PBR, therefore re-configuration and re-calibration of the sensor will be necessary if it were to be integrated into other culture systems.

As another example, Marxen et al. [*J Appl Phycol.* 2005, 17(6), 535-549] developed a bioreactor system for the cultivation of *Synechocystis* sp. PCC6803. Dry mass of microalgae was estimated by the measurement of optical density of the suspension at 870 nm in situ. Chlorophyll concentration was determined by the pulse amplitude modulation (PAM) technique. Since Marxen utilizes a specific bioreactor system, any sensor from Marxen may be difficult to integrate with other culture systems. Further, Yao et al. [2012 ASABE Paper No. 12-1338431, St. Joseph, Mich.: ASABE] developed and tested an optical density based sensor using a LED and photodiode based unit at two wavelengths (Red and NIR) to monitor algae growth. The sensor was estimated biomass concentration ranging from 0.05 to 0.50 OD in indoor conditions. The study reported temperature dependency of the sensor unit that caused inaccurate measurement of algal biomass concentration when tested in outdoor conditions.

Hence, there is a need for an optical sensor design for in situ monitoring of microorganism systems or streams that allows for measurement of multiple biological parameters in real time within a high cell concentration range, and without requiring sample preparation (i.e. dilution, washing, and filtration) prior to measurements. The present invention features a low cost multi-wavelength laser diode-photodiode based sensor applicable for use in microorganism production systems to monitor optical density and growth of microorganisms in real time. Moreover, since the invention does not require dilution of high cell concentrations, the system can be integrated into any microorganism cultivation system for real time monitoring, which can lead to improved resource use efficiency.

SUMMARY OF THE INVENTION

It is an objective of the present invention to provide for a system for real-time monitoring of microorganism production through the use of a multi-wavelength based optical density sensor unit, as specified in the independent claims. Embodiments of the invention are given in the dependent claims. Embodiments of the present invention can be freely combined with each other if they are not mutually exclusive. A non-limiting example of the optical sensor system may comprise laser diode modules as light sources, photodiodes as detectors, a driver circuit, a flow chamber and a sensor housing temperature controller. The sensor unit can be integrated into any microorganism culture system for both real time and non-real time optical density measurements and growth monitoring applications.

As compared to existing optical sensors, one of the unique and inventive technical features of the present invention is the use of stronger laser diodes and distinct wavelengths. Without wishing to limit the invention to any theory or mechanism, the simultaneous use of these wavelengths advantageously provides for correlation of optical density measurements to biological parameters. In addition, the invention advantageously uses light path lengths that eliminate the need for sample preparation and sample dilution requirements, therefore allowing for real-time measurements. None of the presently known prior references or work has the unique inventive technical features of the present invention.

In an exemplary embodiment, the present invention features an inline multi-wavelength optical sensor system for monitoring of microorganism production. The optical sensor system can comprise a housing, a flow chamber, a plurality of laser diodes for emitting light at particular wavelengths, a plurality of photodiodes for sensing said emitted light, a laser control circuitry operatively connected to the laser diodes, a signal conditioning circuitry operatively connected to the photodiodes, a microprocessor, and a memory for storing instructions that causes the microprocessor to perform certain operations. Optionally, the system may further comprise a data acquisition system for converting voltage signals corresponding to wavelengths into measurements of biological parameters such as cell concentration, turbidity, and chlorophyll content, which are displayed on a graphical user interface and allows a user to monitor measurements in real time.

DESCRIPTION OF PREFERRED EMBODIMENTS

Figure 1:
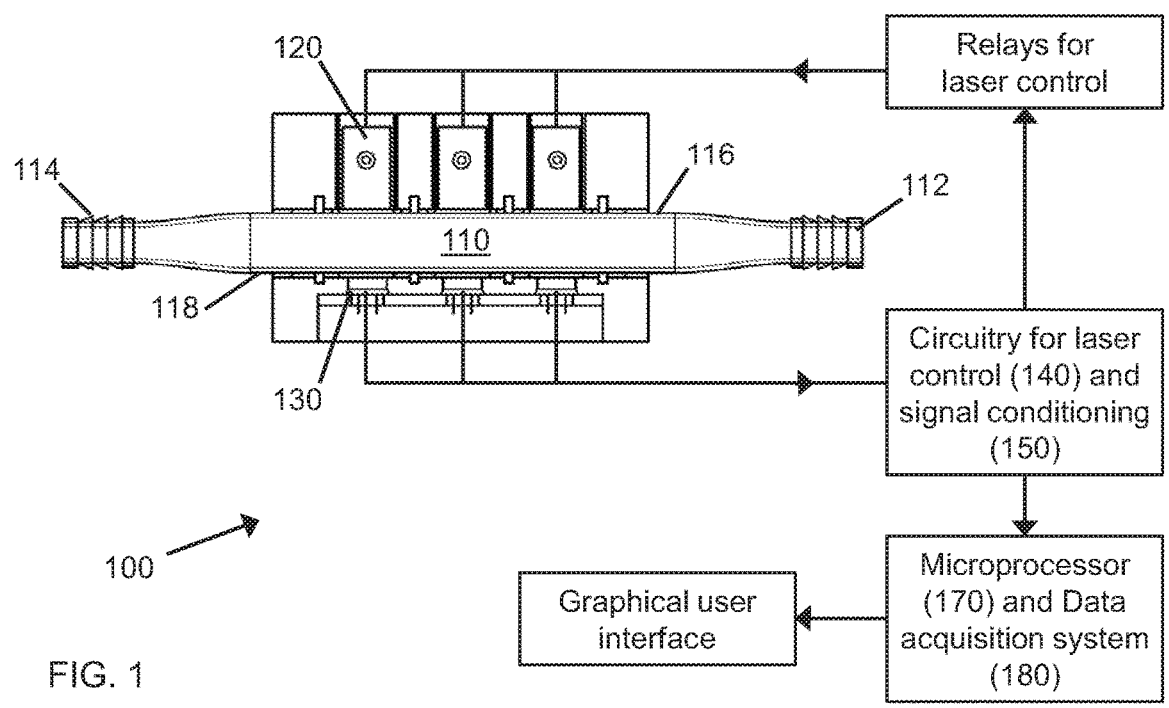
FIG. 1 shows an exemplary schematic of the optical sensor system. Three laser diodes at wavelengths of 650 nm, 685 nm and 780 nm were aligned with 3 photodiodes with a detection range of 350-1100 nm. The flow chamber window was perpendicular to the laser beam.

As used herein, the term "microorganism" refers to microscopic organisms. As known to one of ordinary skill in the art, microorganisms may be divided into seven categories: algae, fungi such yeast and mold, bacteria, archaea, protozoa, viruses, and multicellular animal parasites such as helminths. Non-limiting embodiments of the present invention features systems for monitoring of microalgae and yeast production. More generally, the present invention can be used in monitoring of any microorganism.

Referring now to FIGS. 1-12, the present invention features a multi-wavelength optical sensor system (100) for monitoring microorganism production. The system (100) may comprise a flow chamber (110), a plurality of laser diodes (120), one or more photodiodes (130), a laser control circuitry (140) operatively connected to the laser diodes (120), a signal conditioning circuitry (150) operatively connected to the photodiodes (130), a microprocessor (170), a memory operatively coupled to the microprocessor, and a housing (160). The housing (160) may be configured to hold the flow chamber (110), laser diodes (120), and photodiodes (130), the laser control circuitry (140), and the signal conditioning circuitry (150). Preferably, the housing (160) removeably attaches to and fluidly mates with a microorganism production chamber such that a microorganism culture flows through the flow chamber (110). An exemplary embodiment of the housing is a chassis for the laser diodes (120), photodiodes (130), and flow chamber (110). The system may further comprise optical filters for the laser diodes (120), and the optical filters may be placed in the chassis. In one embodiment, the housing (160) may be a square aluminum tube. However, any suitable shape and material may be used for the housing (160) when practicing the invention.

In some embodiments, the flow chamber (110) has an inlet (112), an outlet (114), a first side (116), and a second side (118) that may be opposite of the first side (116). The microorganism culture can be pumped through the flow chamber (110), flowing from the inlet (112) to the outlet (114) of the flow chamber, via a sampling pump. The sampling pump can be activated by a separate power switch or a microprocessor. In other embodiments, portions of the flow chamber (110) may be transparent where the laser diodes (120) and photodiodes (130) are placed. For example, the flow chamber (110) may be constructed from metal and have ports at the locations of laser diodes (120) and photodiodes (130). In still other embodiments, the flow chamber (110) is constructed from a substantially transparent material, such as a transparent polymer or glass material. In some embodiments, the flow chamber (110) is a rectangular or square flow cell. Preferably, the flow chamber (110) may be in any suitable shape that allows for an aligned and certain path length for light transmission to be achieved. Other configurations of the flow chamber (110) can include cylinders and rectangular prisms. The flow chamber (110) may further comprise inlet lines and outlet lines that are connected to its inlet (112) and outlet (114) respectively. In one embodiment, the flow cell (110) may be a square glass tube (such as about 5 mm inner and 6.4 mm outer width) with its inlet and outlet ends shaped for tubing connection. Non-limiting examples of such lines may include plastic tubing or pipe such as PVC.

As used herein, one of ordinary skill in the art will understand that the term "light path length" is defined as the distance between a light emitter and a light collector. As a non-limiting example, the path length may be the distance that light travels through a sample in a cuvette/cell. In preferred embodiments, the flow chamber (110) can have a light path length effective for providing voltage signal readings that are converted into measurements of biological parameters without requiring sample preparation or sample dilution of the microorganism culture. For instance, one embodiment of the present invention may have a path length of about 5 mm or about 10 mm, which is common in spectrophotometers. The flow chamber (110) can have a light path length that ranges from about 3 mm to 20 mm, or about 5 mm to 15 mm. For example, the light path length may be about 5 mm or about 10 mm in the flow chamber (110).

In other embodiments, the plurality of laser diodes (120) may comprise about 2 to 5 laser diodes. For instance, the laser diodes (120) comprise at least three laser diodes. In another embodiment, the plurality of laser diodes (120) may be disposed on the first side (116) of the flow chamber and oriented in a manner to allow for light to transmit into the flow chamber (110). For example, the laser diodes (120) are perpendicularly oriented relative to the flow chamber (110). In another embodiment, the laser diodes (120) are linearly aligned along the length of the flow chamber (110). As known to one of ordinary skill in the art, a laser diode (120) can emit light at a wavelength having about a 10 nm span.

As used herein, the center wavelength is the mean of a lower wavelength and an upper wavelength. For example, a laser diode emitting wavelengths in the 680 to 690 nm range has a center wavelength of 685 nm. In some embodiments, each laser diode (120) can emit light at a center wavelength. Preferably, the light emitted by the laser diodes is collimated. In one embodiment, each laser diode (120) emits light at a particular center wavelength which differs from center wavelengths of the other laser diodes (120). In some embodiments, the laser diodes (120) may be selected to emit light at a plurality of wavelengths effective for measuring biological parameters. For example, in microalgae monitoring, the laser diodes (120) are selected to emit light at wavelengths effective for measuring turbidity, cell concentration, and chlorophyll concentrations. A first laser diode, a second laser diode, and a third laser diode can emit light at center wavelengths of approximately 650, 685, and 780 nanometers respectively. The optical densities at these wavelengths are good indicators of biomass concentration as well as health condition of green microalgae. However, it is understood that the present invention is not limited to the wavelengths described herein, and that any laser/photo diode arrangement with other wavelengths of interest may be utilized for unique applications. For instance, other wavelengths (e.g. 540 nm and 830-860 nm) may be used for biomass concentration measurement of other species of microorganisms.

In some embodiments, the one or more photodiodes (130) may be oriented in a manner so as to receive the light emitted from the laser diodes (120) and passing through the flow chamber (110). In other embodiments, the photodiodes (130) are linearly aligned along the length of the flow chamber (110). The number of photodiodes can range from about 1 to 5 photodiodes (130). In one embodiment, the plurality of photodiodes (130) comprises at least three photodiodes. In another embodiment, the number of photodiodes is equal to the number of laser diodes (120) such that each photodiode (130) and laser diode (120) forms an optical sensor pair. For example, a non-limiting embodiment may feature a first photodiode, a second photodiode, and a third photodiode. The first photo diode can detect light from the first laser diode, the second photo diode can detect light from the second laser diode, and the third photodiode can detect light from the third laser diode.

In one embodiment, the photodiodes (130) may be disposed on or near the second side (118) of the flow chamber (110) opposite from the laser diodes (120). In another embodiment, the photodiodes (130) are disposed on or near the first side (116) of the flow chamber (110). In a further embodiment, the photodiodes (130) are disposed on or near the flow chamber (110) at an angle with respect to the laser diodes (120) such that the photodiodes (130) oriented to detect light reflected from the microorganism culture. The angle may range from 0° to less than 180°. For example, the sensor unit may have a 90° arrangement of the laser and photo diodes to enable nephelometer measurement. Preferably, the photodiodes (130) are oriented to detect light transmitted through a medium in the flow chamber (110), such as the microorganism culture. In some embodiments, the photodiodes (130) are sensitive to transmitted light at a plurality of wavelengths corresponding to the plurality of wavelengths of the laser diodes (120). In a preferred embodiment, each photodiode (130) is perpendicularly oriented relative to the flow chamber (110) and directly in line with its corresponding laser diode (120) so as to sense transmitted light at a wavelength corresponding to the wavelength of the laser diode. For example, the photodiodes (130) may be capable of sensing wavelengths ranging from between about 350 to 1100 nanometers.

In some embodiments, a first distance is the distance between each neighboring laser diode (120). Non-limiting examples include distances of between about 0.5 mm to 80 mm, or about 5 to 15 mm, or about 15 to 30 mm. In other embodiments, a second distance is the distance between each neighboring photodiode (130). Non-limiting examples include distances of between about 0.5 mm to 80 mm, or about 5 to 15 mm, or about 15 to 30 mm. For instance, the first and second distances may each be about 15 mm. It is understood that the first and second distances are not limited to the aforementioned distances, and may be any appropriate distance as necessitated by the mechanics and design of the system.

In some embodiments, the laser control circuitry (140) is operatively connected to the laser diodes (120). The laser control circuitry (140) is capable of supplying power to each laser diode (120) upon receiving a control signal. For example, the laser control circuitry (140) can activate and deactivate (i.e. turn on and off) each laser diode (120) individually to prevent light noise. In other embodiments, the signal conditioning circuitry (150) is operatively connected to the photodiodes (130). The signal conditioning circuitry (150) can receive signals from the photodiodes (130), and then amplify the signals by a zero bias amplification circuitry.

In some embodiments, a microprocessor (170) may be operatively connected to the laser control circuitry (140) and the signal conditioning circuitry (150). In one embodiment, the microprocessor (170) may be disposed in the housing (160). Alternatively, the microprocessor (170) may be disposed in a data acquisition system (180). The memory can be operatively coupled to the microprocessor (170), and store computer-readable instructions that, when executed by the microprocessor, cause the microprocessor to perform operations. These operations may comprise generating the control signal for the laser control circuitry (140), wherein the laser control signal activates at least one of the plurality of laser diodes (120) corresponding to at least one of the plurality of wavelengths of the laser diodes, reading at least one voltage signal from the signal conditioning circuitry (150) corresponding to at least one of the photodiodes (130) sensitive to the at least one wavelength of the activated laser diodes, and recording the voltage signals corresponding to the activated wavelengths. The operations may further comprise reporting the data on the graphical user interface.

In other embodiments, the system may further comprise a data acquisition system (DAQ) (180) operatively connected to the microprocessor (170), which is configured to send the voltage signals and corresponding wavelengths to the data acquisition system (180). The data acquisition system (180) can convert the voltage signals into measurements voltage signals into measurements of one or more biological parameters, such as turbidity, cell concentration, and chlorophyll concentrations for microalgae monitoring. For example, a first wavelength (780 nm) correlates to turbidity whereas a second (650 nm) and a third wavelength (685 nm) correlates to cell concentration and chlorophyll content. The data acquisition system (180) may also send commands to the laser control circuitry (140) to turn on each laser diode (120) individually. Preferably, the data acquisition system (180) comprises a graphical user interface that allows a user to monitor measurements in real-time. In still further embodiments, the conversion is calibrated to known readings from a second instrument (i.e. a benchtop spectrophotometer). Preferably, the optical sensor system (100) is compatible with, and configured to be integrated into, any data acquisition system that accepts and measures voltage inputs.

Alternative embodiments of the present invention where the measurements are dependent on temperature may further comprise a temperature controlling means, such as a fan, a cooling device, or a heating unit, for maintaining a temperature of the laser and/or photo diodes. For example, in one embodiment, the system (100) may further comprise a stand-alone temperature control module for setting and controlling the temperature of the lasers. In one embodiment, the temperature control module may be disposed in the housing. A circuit board for signal amplification and laser voltage adjustment can serve as a mounting chassis for a temperature control board. Alternatively, the temperature control module may be separate from the housing. In other embodiments, the measurements of the system are independent of the temperature of the laser diodes or photo diodes. In still further embodiments, the measurements of the system are independent of the ambient temperature.

Figure 2:
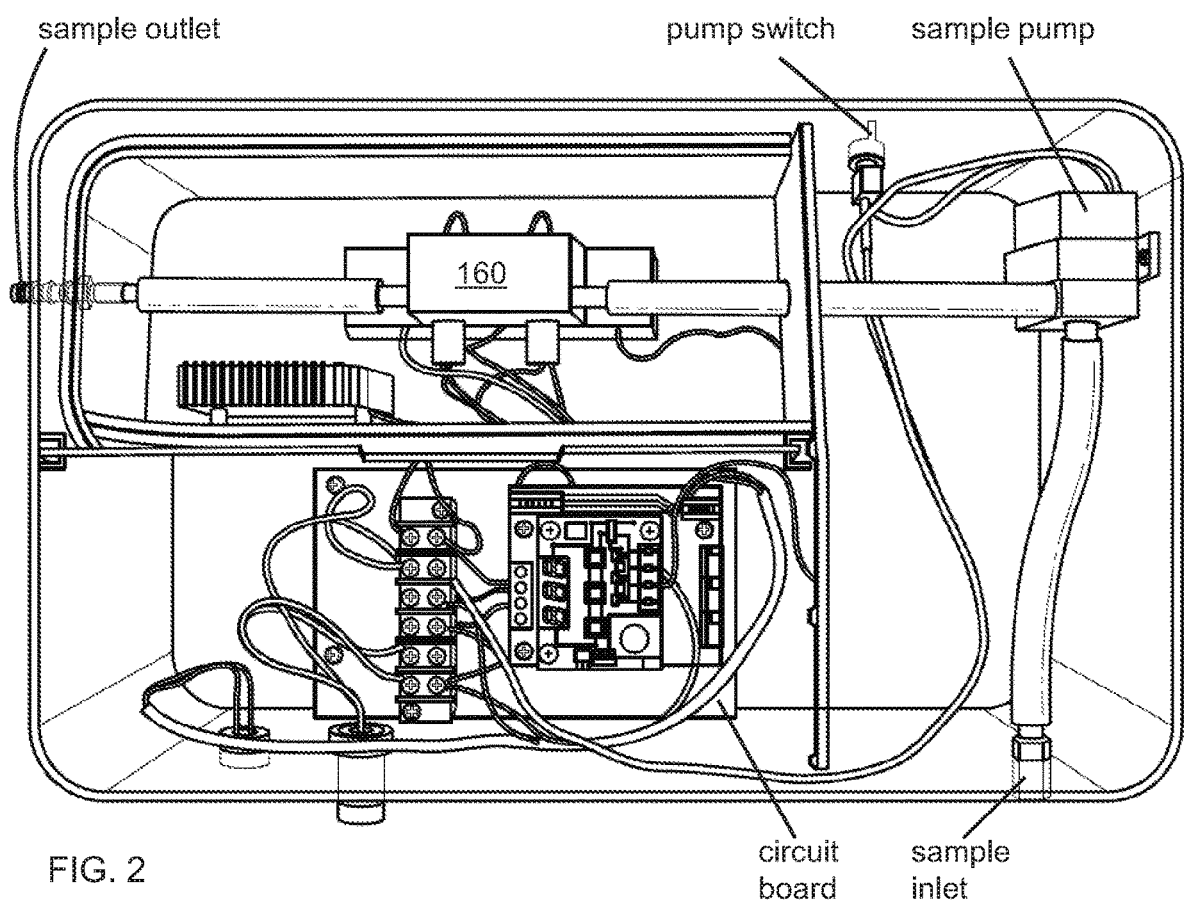
FIG. 2 shows a top view of an exemplary embodiment of the present invention.
Figure 3:
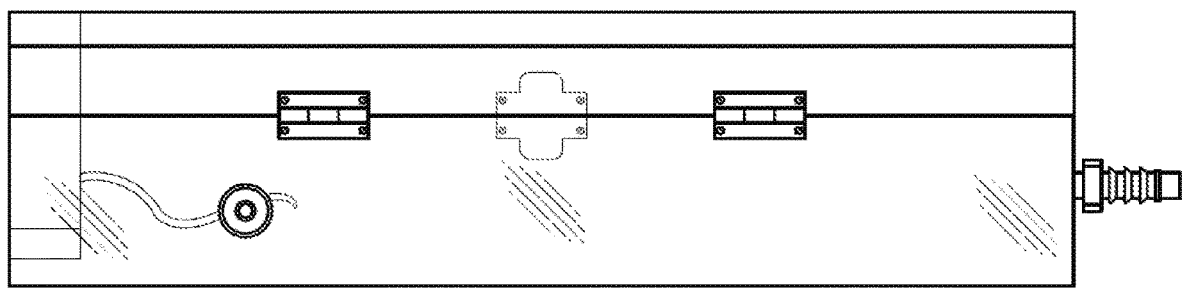
FIG. 3 shows a back view of an embodiment of the present invention.
Figure 4:
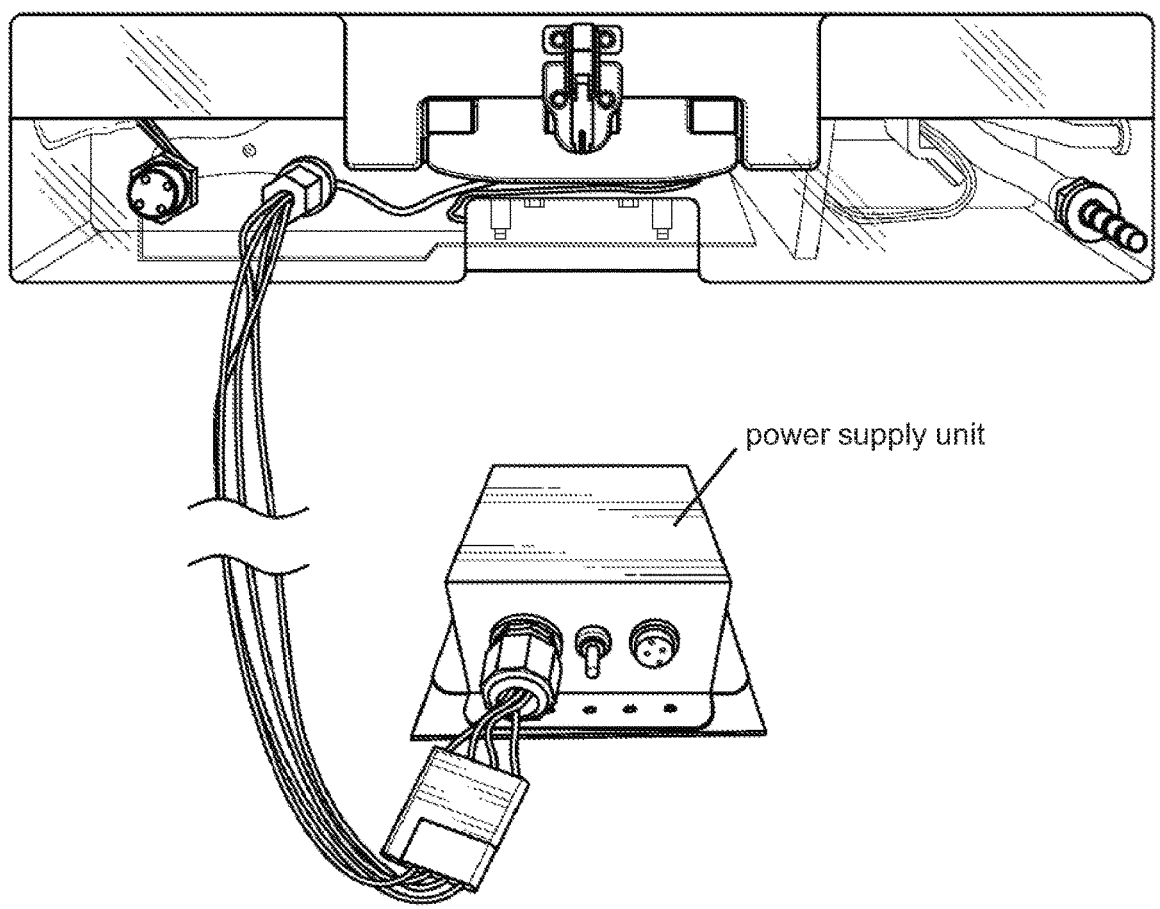
FIG. 4 shows a front view of an embodiment connected to a power supply unit.

Referring to FIG. 2, in some embodiments, the system hardware components, such as the sensor unit, circuit boards, temperature control module, and sample pump may be completely housed in one enclosure to withstand outdoor environmental conditions. The DAQ, tubing for sample circulation, and power supply may be separate from the enclosure. For example, the enclosure may be a rectangular box having a lid with a locking means, such as a catch lock or hasp, to secure the lid to the box. As shown in FIG. 4, in one embodiment, a power switch and power supply unit for the entire system may be physically separated from, but operatively connected to, the main enclosure. In another embodiment, a separate power switch may be used to control the sampling pump as shown in FIG. 3. Preferably, all cable connections and fittings on the enclosure are dust-proof. According to another embodiment, the enclosure may have a separate section or sub-compartment for the electrical components in order to isolate them from the sensor unit to prevent water damage in case of a leak.

EXPERIMENTAL

For illustrative purposes, the following is a non-limiting example of the present invention and utilization thereof in microalgae and yeast applications. It is understood that the invention may be used for other microorganism applications, and is not limited to the embodiments described herein.

Optical Density Measurement Sensor

As shown in FIG. 1, the growth dynamics of the microalgae culture was measured using the real-time optical density sensor of the present invention. Light absorbance of microalgae suspensions at multiple wavelengths correlate to different characters of microalgae cells. The 650, 685 and 780 laser diodes were used in the sensor unit. These three wavelengths have been commonly used to estimate the cell concentration of microalgae suspension. Light absorbance at 780 nm estimates the turbidity of the suspension since the color of microalgae has no effect on the absorbance, whereas, light absorbance at 650 and 685 nm correlates to both intensity of the color (i.e. chlorophyll content) and cell concentration.

In one embodiment, the optical sensor unit may comprise laser diode modules as light sources, a photodiode as a detector and custom-made fixtures to house them. The laser diode modules may comprise laser diodes, a driver circuit and a housing with adjustable optical lenses. An optical filter can be placed in front of the 685 nm laser diode to allow only the light with wavelength from 680 to 690 nm to pass through. The system design enabled adjustment of the output power of the modules by a potentiometer connected to a power source. The photodiodes with a detection range of about 350-1100 nm were connected to a zero-bias amplification circuit. In an exemplary embodiment, three pairs of laser diode modules and photodiodes were placed in a linear pattern in the fixture. Each pair was aligned and placed a distance apart, for instance, about 15 mm apart. The diameter of the circular light beam from the laser diode modules was adjusted to be slightly smaller than the size of detection window on the photodiode. The optical sensor unit was designed to enable measurements from either standard cuvettes or custom made flow chambers with a desired light path length. In one embodiment, the path length may be about 5 mm. Cuvettes and flow chambers were placed perpendicular to the laser beam and about 1 mm away from the window of photodiodes.

When used for real-time monitoring, laser diodes were powered sequentially by the data logger's control module to avoid light noise from individual laser light sources. The voltage generated from the photodiodes was amplified and recorded by a data logger and controller. The entire sensor unit was mounted in a weather proof enclosure enabling connection of tubes for algae flow through the sensor flow cell and signal cables for the laser diodes and photo diodes. The voltage output of the photodiode is proportional to the intensity of incident light. According to Beer-Lambert law, the light absorbance of the sample was determined by:

$$Abs = -\ln(V_s/V_b)$$

wherein Abs is the light absorbance, $V_b$ is the output of the photodiode from growth media (mV), and $V_s$ is the output of the photodiode from a sample (mV).

Cultivation Conditions and Organisms
Indoor Photobioreactor (PBR) Cultivation:

*Chlorella sorokiniana* (DOE 1412) was cultivated in local well water enriched with Peters professional 20-20-20 general purpose water soluble fertilizer 0.26 g $L^{-1}$, Citraplex 20% iron 0.053 g $L^{-1}$, and trace elements solution ($H_3BO_3$ 0.0029 g $L^{-1}$, $MnCl_2.4H_2O$ 0.0018 g $L^{-1}$, $ZnSO_4.H_2O$ 0.00014 g $L^{-1}$, $Na_2MoO_4.2H_2O$ 0.00039 g $L^{-1}$, $CoCl2.6H_2O$ 0.000055 g $L^{-1}$) under illumination intensity of 200 μmol $m^{-2}$ $s^{-1}$ or 400 μmol $m^{-2}$ $s^{-1}$ in rectangular air lift photo bioreactors (PBRs). The algae culture temperature was light intensity dependent and was stabilized at 30±2° C. The pH of the medium was controlled at 7±0.3 by injecting $CO_2$ from a pressurized liquid $CO_2$ tank into PBRs.

Outdoor Open Pond Raceway Cultivation:

*Scenedesmus obliquus* was used in the outdoor open pond raceway cultivation experiments. *Scenedesmus obliquus* was cultivated in local well water enriched with Pecos medium, trace metal solution and 5 g $L^{-1}$ NaCl. The Pecos medium contained 0.1 g $L^{-1}$ urea (($NH_2$)$_2$CO), 0.012 g $L^{-1}$ $MgSO_4.7H_2O$, 0.035 g $L^{-1}$ $NH_4H_2PO_4$, 0.175 g $L^{-1}$ Potash (KCl), 0.0054 g $L^{-1}$ $FeCl_3$ and 0.02 g $L^{-1}$ $Na_2CO_3$. The culture was maintained in an open pond paddle wheel raceway with a surface area of 3 $m^2$ located in Tucson, Ariz., USA. The culture depth was maintained at 10 cm and increased to 15 cm later in the experiment. The pH of the medium was controlled at 8±0.05 by injecting 95% $CO_2$ through an air sparger.

Offline Biomass Concentration Measurement

Biomass concentration of microalgae was determined by both cell counting and ash-free dry weight (AFDW) measurements. Cell suspension was diluted to a concentration between $10^6$ and $10^7$ cells $mL^{-1}$ for cell counting by a neubauer chamber hemocytometer under a microscope. The AFDW of the cells was measured following methods known to one skilled in the arts. The light absorbance of the cells suspension was measured at 650, 685, 750 and 780 nm by a spectrophotometer using a 10 mm light path length cuvette. Samples were diluted with deionized water when necessary to keep the absorbance reading below 0.5.

Figure 6:
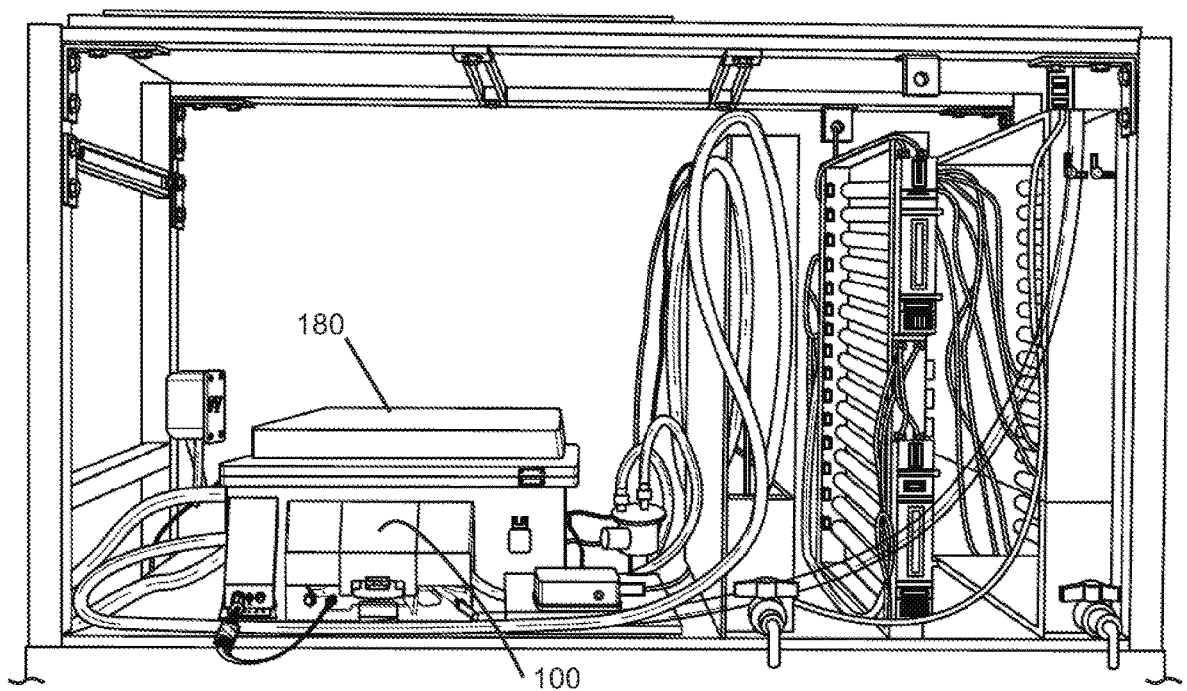
FIG. 6 shows a multi-wavelength optical sensor integrated into air-lift flat panel photobioreactors (PBRs) for real-time microalgae growth monitoring.

Real-Time Monitoring of Microalgae Growth Dynamics
Indoor PBR Cultivation:

The microalgae culture system comprises an air lift flat panel PBR illuminated by a lighting system. The pH, electrical conductivity, dissolved oxygen and thermocouple temperature probes were placed in the PBR for monitoring and control by a datalogger. Each sensor was scanned every second and 10 minute averaged data was stored in the datalogger. Flat panel PBRs were built using clear acrylic panels. Air was constantly injected into the PBR via an air sparger mounted at the bottom of PBR for aeration and to achieve proper mixing of the microalgae culture. Carbon dioxide injection was controlled by the datalogger to maintain a desired pH level (about 7) in the PBR. In one embodiment, the lighting system comprises about fluorescent light tubes mounted on a supporting structure. Two levels of light intensity (200 and 400 μmols $m^{-2}$ $s^{-1}$) were achieved by adjusting the number of lights used. The light remained on 24 hours per day, no dark period was used. A centrifugal pump was used to re-circulate cell suspension through the inline optical density measurement unit for the PBR. As shown in FIG. 6, the optical density sensor was connected to the PBR system for continuous monitoring of OD and microalgae growth.

Figure 5:
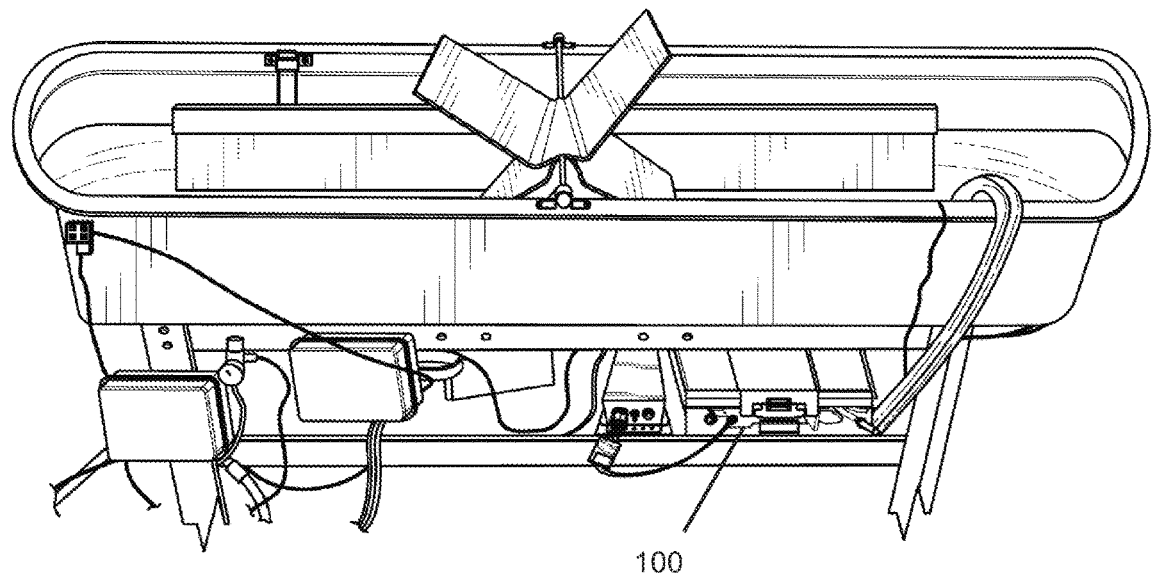
FIG. 5 shows an optical sensor integrated into an open pond raceway for real-time microalgae growth monitoring.

Outdoor Open Pond Raceway Cultivation:

As shown in FIG. 5, the optical density sensor was also integrated into an outdoor raceway system for continuous monitoring of microalgae growth. Since sensor electronics maybe sensitive to environmental conditions, the optical sensor with its housing and the datalogger were placed in a location at the outdoor raceway site to minimize direct exposure to sunlight. The laser output is also temperature dependent (5-15 mV/° C., vary with lasers). Therefore, a temperature control unit was installed and comprised a heater plate and heat sink, such as a Fan Heatsink, to maintain a constant temperature (about 25° C.) inside the sensor box. This also ensured a constant laser power output. The paddle wheel in the raceway system was operated 24 hours a day for continuous culture mixing. The $CO_2$ injection was turned off during night time. In addition to the measurement data collected for the indoor experiment, photosynthetically active radiation (PAR) was also measured using a quantum sensor at the level of the raceway system. All variables were recorded at the same frequency for sensor scanning and data averaging as described for the indoor cultivation experiment. The experiment occurred from 2/25 to 3/15 for a total of 18 days.

Alternative Sensor Applications
Yeast Cultivation:

*Saccharomyces cerevisiae* was cultivated in yeast growth media using a benchtop fermenter. One liter of yeast growth media consisting of 100 ml of salt solution (1 g $CaCl_2$ $2H_2O$, 1 g NaCl, 5 g $MgSO_4.7H_2O$, 10 g $KH_2PO_4$, 50 g $(NH_4)_2SO_4$ solved in 1 liter $H_2O$), 1 ml of trace metal solution (50 mg boric acid, 4 mg copper sulfate.$5H_2O$, 10 mg potassium iodide, 20 mg ferric chloride.$6H_2O$, 40 mg manganese sulfate.$H_2O$, 40 mg sodium molybate.$2H_2O$, 20 mg zinc sulfate.$7H_2O$ solved in 100 ml H2O), 1 ml vitamin and 100 ml of glucose (20%) and water was used to grow yeast. The yeast inoculation concentration was 0.1 g/L. The culture temperature and pH were set to and regulated at 30° C. and 5.0 by the fermenter, respectively. The experiment was terminated after the yeast culture entered the stationary growth phase.

Yeast culture suspension was circulated through the inline OD sensor continuously by a small centrifugal pump. Optical density at 650 and 780 nm was measured every second, and a 5 minute average was recorded by a datalogger. The optical density of the yeast suspension was measured at 650 and 780 nm by a spectrophotometer using a 10 mm light path length cuvette. Samples were diluted with deionized water when necessary to keep the absorbance reading below 0.5. Various samples were taken at different phases of the yeast cultivation for the calibration of the inline OD sensor. The OD measured from benchtop spectrophotometer at the two wavelengths was plotted against OD measured at the point of sampling. Linear calibrations were obtained for both wavelengths.

Results and Discussion

In Situ Calibration of the Optical Density Measurement Unit

Light absorbance from a flowing cell suspension can be different from static samples due to cell movement and potentially the presence of fine air bubbles. Therefore, a calibration of the unit using flowing microalgae culture is necessary. In order to achieve in-line real-time monitoring, sample preparation needs to be eliminated or automated. In the present invention, flow chambers with specific light path lengths, such as 5 mm and 10 mmm, were used to extend the measurement range of the unit without requiring sample dilution.

Figure 7B:
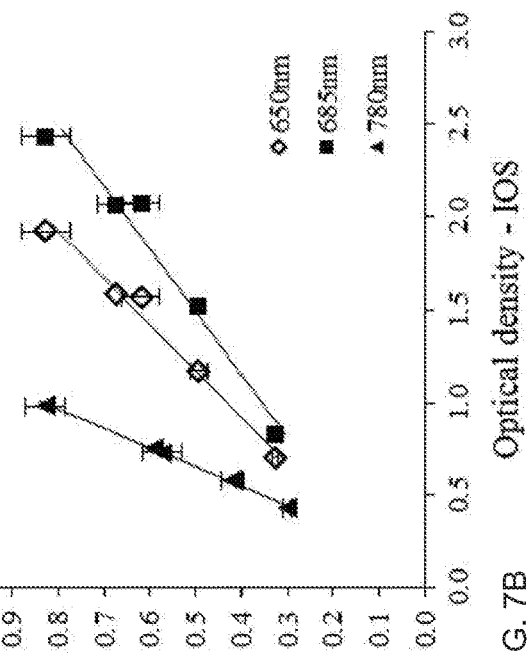
FIG. 7B shows a correlation between optical density (IOS) and AFDW, AFDW=$0.96 \times OD_{780\ (IOS)}-0.12$ ($R^2=0.99$); AFDW=$0.40 \times OD_{650\ (IOS)}+0.032$ ($R^2=0.98$); AFDW=$0.30 \times OD_{685\ (IOS)}+0.061$ ($R^2=0.96$).
Figure 7A:
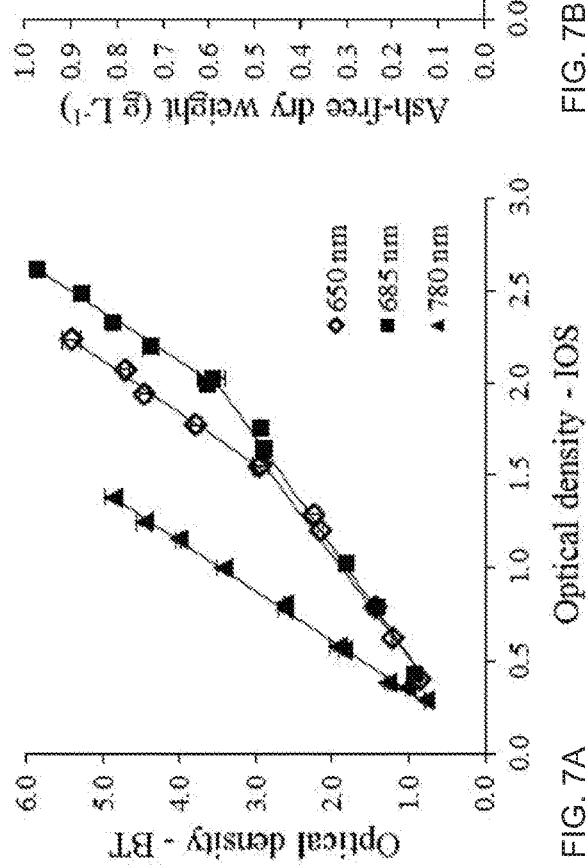
FIG. 7A shows a correlation between the optical densities of *Chlorella sorokiniana* (DOE 1412) in the PBR measured by a bench-top spectrophotometer (BT) and by the inline optical sensors (IOS). $OD_{650\ (BT)}=1.82 \times OD_{650\ (IOS)}+0.056$ (AFDW<0.592 g $L^{-1}$); $OD_{658\ (BT)}=1.70 \times OD_{685\ (IOS)}+0.11$ (AFDW<0.592 g $L^{-1}$); $OD_{650\ (BT)}=3.54 \times OD_{650\ (IOS)}-2.51$ (0.592 g $L^{-1}$<AFDW<1.05 g $L^{-1}$); $OD_{685\ (BT)}=3.72 \times OD_{685\ (IOS)}-3.88$ (0.592 g $L^{-1}$<AFDW<1.05 g $L^{-1}$); and $OD_{780\ (BT)}=3.71 \times OD_{780\ (IOS)}-0.2445$ (AFDW<1.05 g $L^{-1}$).

As shown in FIG. 1, the optical sensor unit (referred as IOS hereafter) was calibrated by comparing the reading from the sensor unit to that from a bench-top spectrophotometer (referred as BT hereafter) at 650, 685 and 780 nm. The bench-top spectrophotometer was calibrated to both ash-free dry weight (AFDW) and cell count (CC) for $C.$ $sorokiniana$ at all three wavelengths: AFDW=0.188*$OD_{650}$+0.0453 g $L^{-1}$ ($R^2$=0.96); AFDW=0.161*$OD_{685}$+0.0292 g $L^{-1}$ ($R^2$=0.96); AFDW=0.205*$OD_{780}$+0.0546 g $L^{-1}$ ($R^2$=0.95); CC= (28.6*$OD_{650}$+1.13) $10^6$ cells $mL^{-1}$ ($R^2$=0.91); CC= (26.8*$OD_{685}$−3.92) $10^6$ cells $mL^{-1}$ ($R^2$=0.95); and CC= (29.8*$OD_{780}$+3.96) $10^6$ cells $mL^{-1}$ ($R^2$=0.90). The optical density readings measured from the spectrophotometer using standard 10 mm cuvettes were compared to the results obtained from optical sensor unit using the 5 mm flow cell. Strong linear correlations between the two measurement units were obtained at all wavelengths examined (FIGS. 7A and 7B). A linear correlation was tightly followed ($R^2$=0.99) between the optical density measurements obtained from IOS and BT units at 780 nm with cell concentration up to 1.05 g $L^{-1}$ (1.51×$10^8$ cells $mL^{-1}$). Linear correlations hold for $OD_{650}$ ($R^2$=0.98) and $OD_{685}$ ($R^2$=0.99) for cell concentrations below 0.592 g $L^{-1}$. However, beyond this range and while below 1.05 g $L^{-1}$, different linear correlations were observed for these two wavelengths. Compared to the results from Nedbal et al., the optical sensor unit showed the capability of measuring cell concentration over a wide range without dilution of the samples. The same calibration procedure was performed for $S. obliquus$ during outdoor testing.

Figure 8:
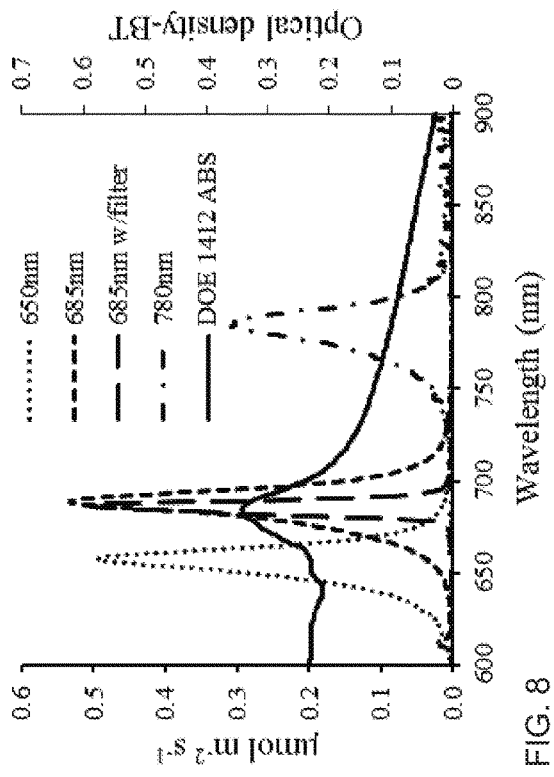
FIG. 8 shows a light absorbance spectrum of DOE 1412 and light spectra of laser diodes used on the optical sensor.

The OD readings from the optical sensor unit measured using 5 mm path length flow cell should be half of that from the spectrophotometer using a standard 10 mm cuvette in theory. However, the results did not show an exact correlation between the two units. This was due to the light quality from the laser diodes not being the same as that in a spectrophotometer where a monochromatic light was generated. FIG. 8 shows the spectra of the laser diodes used in the developed sensor unit, measured by a spectroradiometer and the optical density spectra of DOE 1412. The peak wavelengths of each laser diode were slightly shifted from what was claimed by the manufacturers. An optical filter was used to narrow the band width of 685 nm laser diode from 80 nm to 10 nm and corrected the peak wavelength back to 685 nm from 688 nm. Despite the inferiority of the light beam generated from laser diodes, the strong linear correlations proved that the optical sensor unit was able to estimate the cell density as accurate as a spectrophotometer via calibration (FIGS. 7A and 7B).

Real-Time Microalgae Growth Monitoring

Figure 9A:
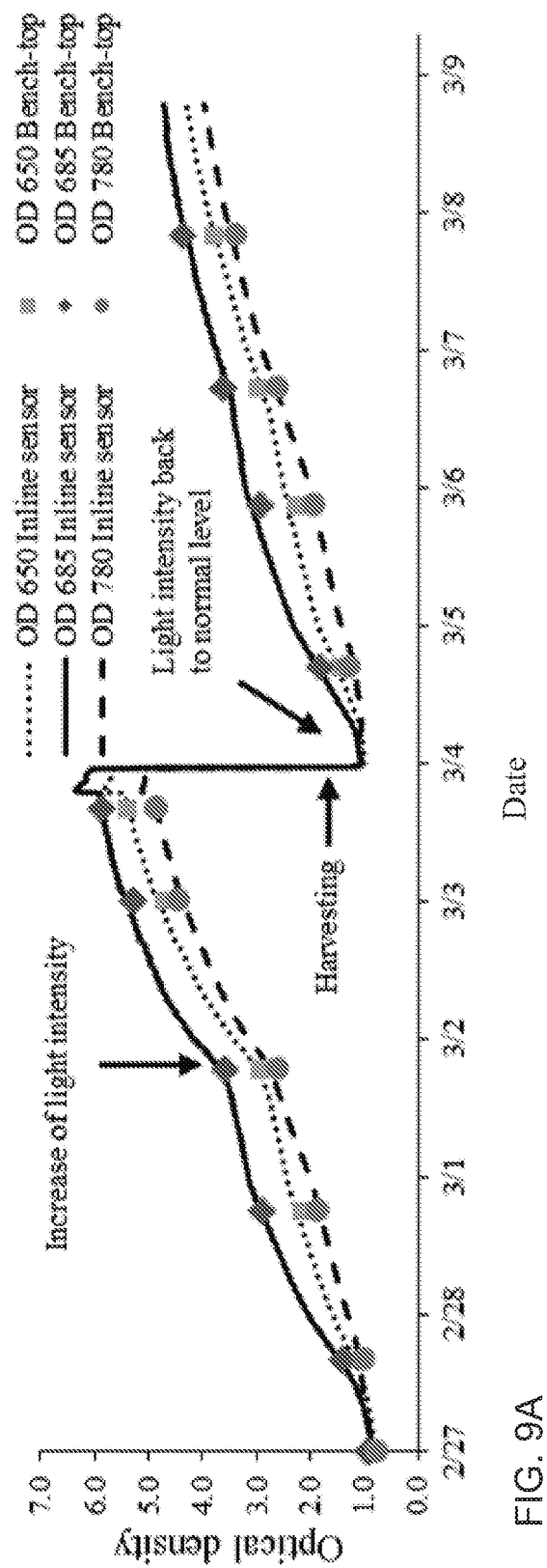
FIG. 9A shows dynamics of optical density at 650 nm, 685 nm and 780 nm during semi-continuous culture of DOE 1412 run for 10 days. Illumination intensity was increased from 200 µmol $m^{-2}$ $s^{-1}$ to 400 µmol $m^{-2}$ $s^{-1}$ during the first batch on 3/2; it was then reduced to 200 µmol $m^{-2}$ $s^{-1}$ by the end of the batch.

The optical sensor unit along with other sensors to monitor algae culture environment was integrated into a PBR to monitor the dynamics of a microalgae culture system. FIG. 9A shows the growth dynamics of semi-continuous culture of DOE 1412 as measured by the optical sensor unit over a period of 10 days. Sensor output shown in FIG. 9A was calibrated to optical density reading from a bench-top spectrophotometer. The optical sensor unit showed the capability to capture the growth phases during semi-continuous operation, and the sudden change of cell concentration due to harvesting and addition of fresh media (indicated with arrows on the figure). A maximum cell concentration of 1.05 g $L^{-1}$ (1.51×$10^8$ cells $mL^{-1}$) was observed during the cultivation experiment without any sample preparation and dilution for the measurements. Growth dynamics of the microalgae was quantified by the growth rate. The growth rate was determined by the following equation with Δt of 2 hours (0.08 days):

$$\mu = \frac{\ln(OD_2)_\lambda - \ln(OD_1)_\lambda}{\Delta t}$$

wherein μ=Growth rate ($day^{-1}$), OD=Optical density of microalgae at different time points (λ=780 nm), and Δt=Difference between the two time points (day).

Figure 9B:
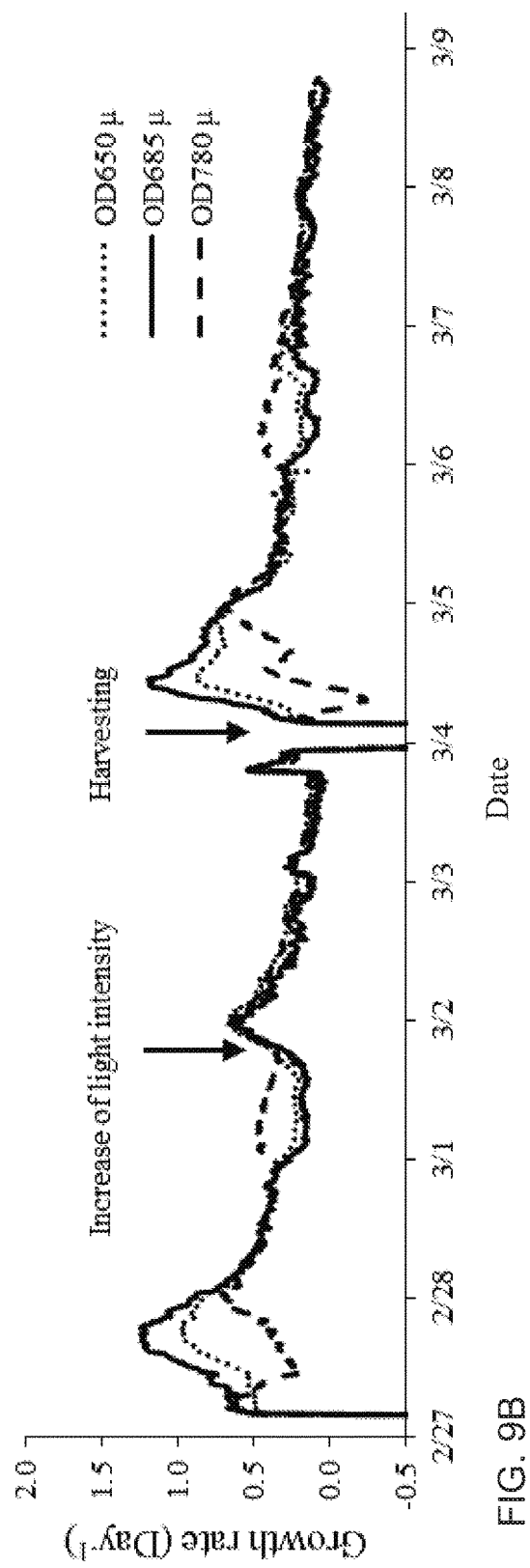
FIG. 9B shows a growth rate of DOE 1412 at 650, 685 and 780 nm.

The change of growth rate was clearly demonstrated by plotting the growth rate (μ) of DOE 1412 over time (FIG. 9B). The initial lag phase was followed by an increase in cell growth. Microalgae culture reached maximum growth rate soon after the lag phase when there is no light limitation. The growth rate then gradually decreases as the culture becomes light limited. When the illumination intensity was increased from 200 μmol $m^{-2}$ $s^{-1}$ to 400 μmol $m^{-2}$ $s^{-1}$ on Mar. 2, 2014, an increase in growth rate was observed (FIG. 9B). The growth rate dropped down to the level prior the alternation of light intensity as the culture again became light limited. These events were detected by the optical sensor unit (FIG. 9A and FIG. 9B). Although real time growth rate is not required for microalgal biomass production purposes, data with such high resolution provided a useful tool for studying the fast response of microalgae to sudden change of the environmental conditions.

Figure 9C:
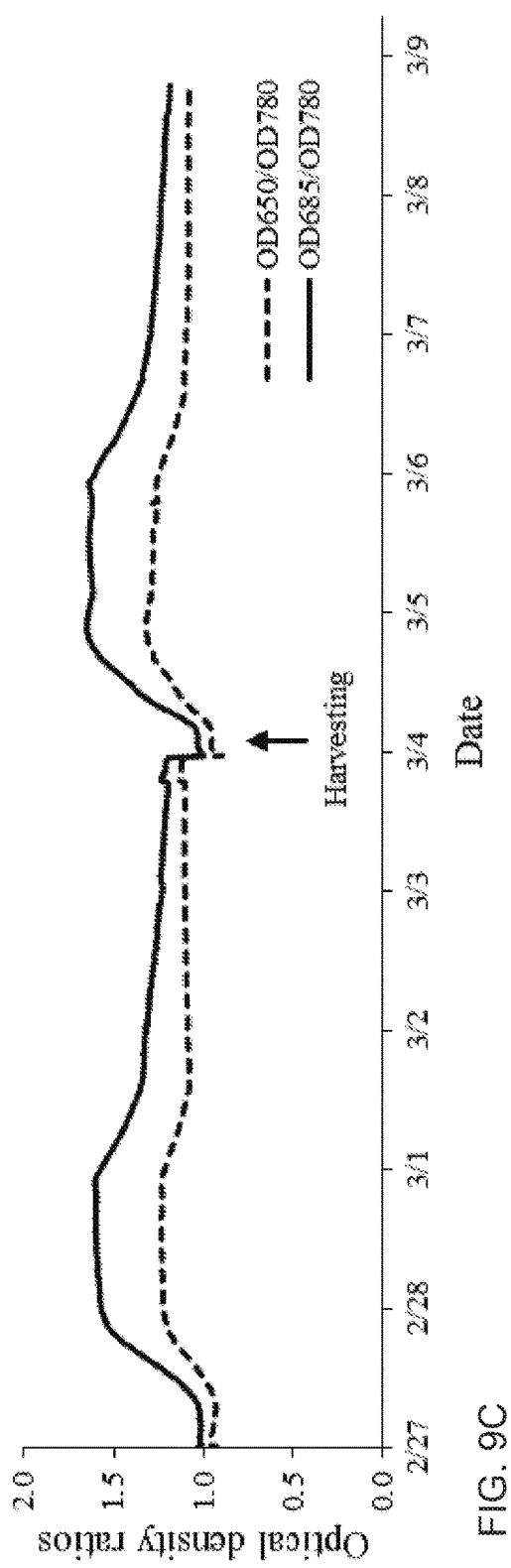
FIG. 9C shows ratios of optical densities at 650/780 nm and 685/780 nm for monitoring algae growth and health.
Figure 10:
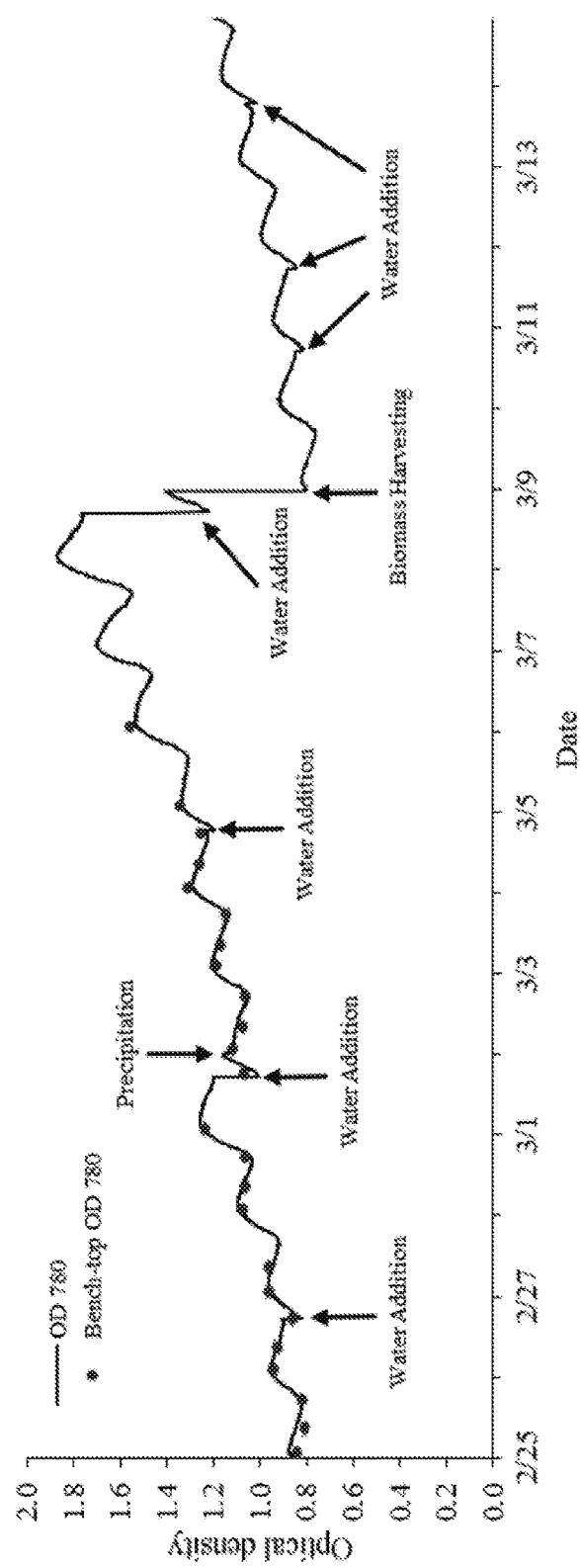
FIG. 10 shows an optical density change of *S. obliquus* in open pond raceway over 18 days. Black arrows indicate events of water addition, precipitation and biomass harvesting.

Monitoring not only the cell concentration change, but also the dynamic physiological status of the microalgae culture including the changes in growth rate and the change of chlorophyll content can serve as indicators of the health of the culture. This is important for cultivation of microalgae production when it is desirable to control conditions to produce a product of interest. For example, some microalgae produce more lipids when nutrients, such as nitrogen, are limiting. The ratios of optical densities at different wavelengths (685/780 nm and 650/780 nm) are shown in FIG. 9C. The ratios remained constant during lag phase, followed by a rapid increase during the exponential growth phase and stabilized at a higher level throughout the linear growth phase. The ratios then started to decrease as the cell growth slowed down, which indicated the transition from linear to stationary phase. The pattern of the ratio change occurred repeatedly over the time course of the experiment regardless of the growth pattern change induced by increased light intensity during the first batch. Signaling of this transition indicated that there is a decrease of chlorophyll content, which absorbs most of the red light during the period indicated by the decreasing optical density ratios. This may be due to nitrogen limitation, since nitrogen is often rapidly consumed by algal cells during exponential growth.

Figure 11A:
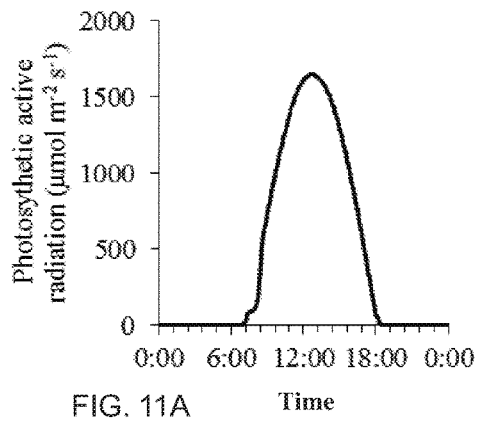
FIG. 11A an exemplary photosynthetic active radiation (PAR) of a sunny day.
Figure 11B:
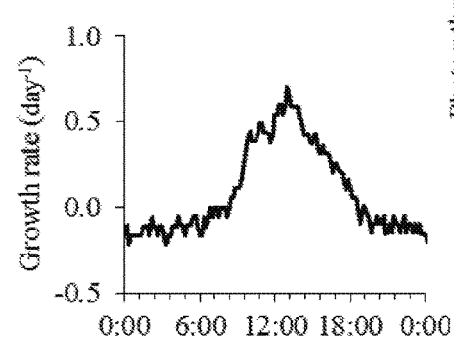
FIG. 11B shows a growth rate (µ) of *S. obliquus* in open pond raceway of the same day for which the PAR data is shown on FIG. 11A.
Figure 11C:
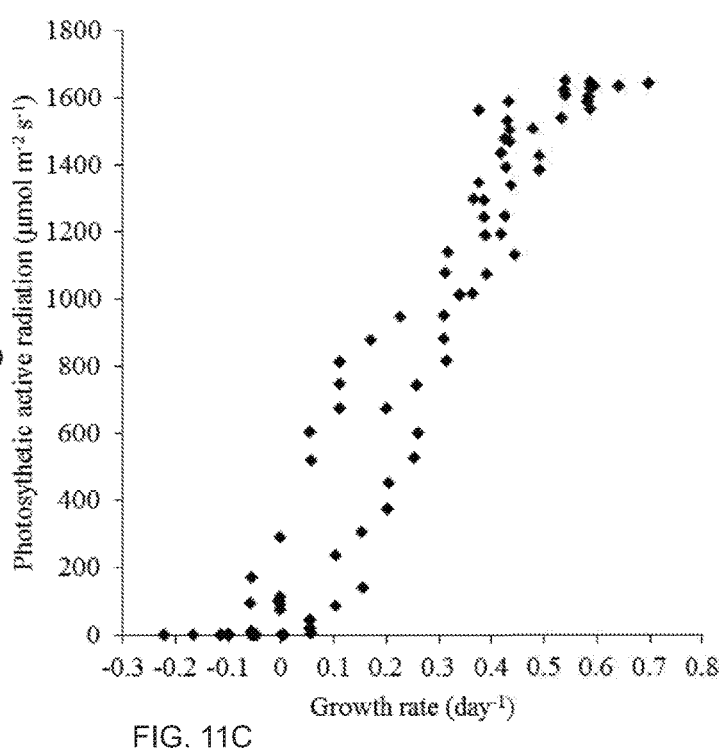
FIG. 11C shows a scattered plot of PAR and µ from the data presented in FIG. 11A and FIG. 11B.

The optical sensor unit was also integrated into an outdoor open pond raceway for stability testing under highly dynamic outdoor weather conditions such as large temperature variations between daytime and nighttime periods. For instance, a 20° C. temperature difference were measured inside sensor box from daytime to nighttime when the temperature control system was not activated. The optical density of the culture of S. obliquus during a period of 18 days recorded by the optical sensor is shown in FIG. 8. The real-time optical density shows repeatedly an increase OD reading indicating the biomass increase during the day time due to photosynthesis. A small decrease in optical density was observed during the nighttime since photosynthetic microorganisms metabolize intracellular carbohydrate to sustain their metabolic activity. Sudden decreases of optical density of the culture due to water addition, precipitation (rain) and biomass harvesting were clearly shown in the figure labeled by arrows. The growth rate of S. obliquus was compared to photosynthetic active radiation (PAR) measured at the raceway (FIG. 11). The growth rate of S. obliquus was dependent on the PAR level except during the water addition time period. This set of high resolution data enables one to evaluate in detail about how S. obliquus responds to solar radiation level in a sunny day. The correlation between PAR and growth rate can be used for the prediction of biomass production rate based on historical weather data for a given region.

The multi-wavelength laser diode based optical sensor unit was designed, developed and evaluated for the monitoring of microalgae culture dynamics in real-time. The optical sensor unit of the present invention demonstrated the capability of estimating cell concentration and changes of the physiological status of the microalgae culture in real-time. The sensor unit was operated continuously for 18 days without any visible microalgae biofilm deposit observed on the flow chamber of the sensor unit. In this design, the only component of the sensor hardware that had contact with the culture medium is the flow chamber, which is easily replaceable. In further embodiments, an ultra-hydrophobic material may be applied on the surface of flow chamber to further extend the maintenance interval.

Algae biomass concentration was accurately estimated by optical density measurements at 650, 685 and 780 nm wavelengths used by the sensor unit. The sensor was capable of measuring maximum optical density of 5.41, 5.86 and 4.88, (e.g. as high as 1.05 g L$^{-1}$ (1.51×10$^8$ cells mL$^{-1}$) at 650 nm, 685 nm and 780 nm respectively without any sample preparation for the measurements. Growth rates and ratios calculated from optical density at each wavelength were good indications for monitoring of microalgae growth transitions and for detection of disturbances to the culture system (i.e. change of light intensity, water addition, rain, and harvesting). With proper calibration, installation and operation, the optical sensor of the present invention can be integrated into any microalgae productions systems, such as PBRs and outdoor raceways, for real-time monitoring purposes at a relative low cost to ultimately help optimize product quality and quantity.

Real-Time Yeast Growth Monitoring

Figure 12:
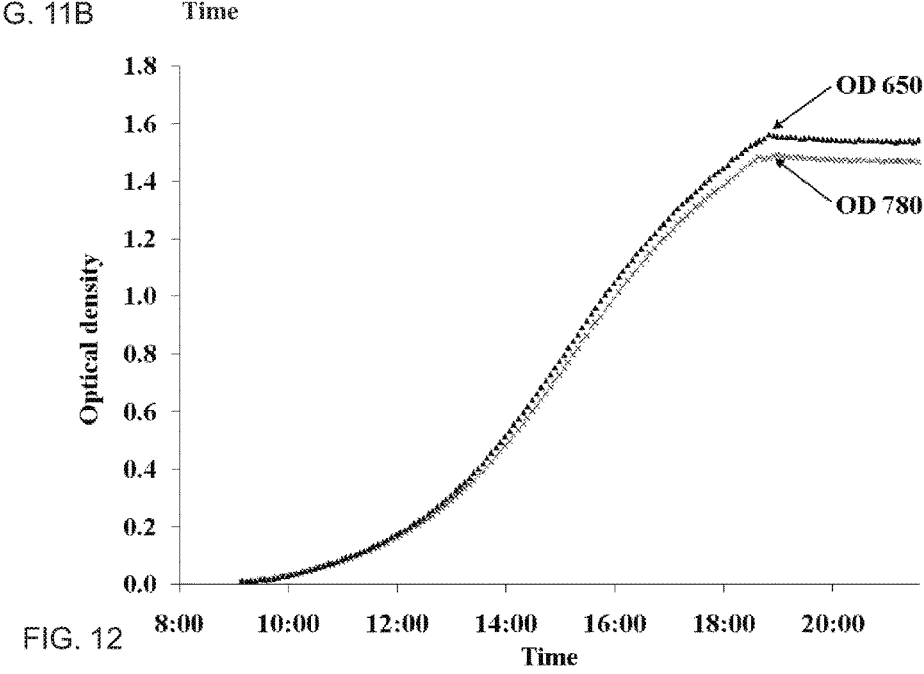
FIG. 12 shows optical density of a yeast bench culture monitored by the inline optical density sensor according to an alternative application of the present invention.

The OD change measured at 650 and 780 nm of a yeast bench culture is shown in FIG. 12. Various growth phases such as lag phase, exponential phase, linear phase and stationary phase were clearly identified and monitored with high resolution using the inline OD sensor.

As used herein, the term "about" refers to plus or minus 10% of the referenced number. Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. An in-line multi-wavelength optical sensor system (100) for monitoring of microorganism production, said system (100) comprising:
   a. a sample comprising a microalgae culture;
   b. a rectangular flow chamber (110) having an inlet (112), an outlet (114), a first side (116) and a second side (118), wherein the flow chamber (110) is configured to fluidly connect to a microorganism production chamber such that the flow chamber (110) is in-line with the microorganism production chamber, wherein the sample comprising the microalgae culture is pumped through the flow chamber (110) from the inlet (112) to the outlet (114), wherein the sample comprising the microalgae culture flows through and contacts only the flow chamber, wherein the inlet (112), the flow chamber (110) and the outlet (114) are all positioned on the same plane such that the flow chamber (110) tapers towards both the inlet (112) and the outlet (114), wherein a diameter of the rectangular flow chamber (110) is 5 to 20 mm to contain the sample comprising the microalgae culture;
   c. a plurality of laser diodes (120) disposed on the first side (112) of the flow chamber, wherein the laser diodes (120) emit light at a plurality of wavelengths, wherein the laser diodes (120) are oriented along a first side of the flow chamber (110) such that light is transmitted into the flow chamber (110) at a right angle to a flow direction, wherein the plurality of wavelengths are configured to generate voltage signals to measure only absorbance in the sample comprising the microalgae culture;

d. a plurality of photodiodes (130) oriented to receive light transmitted from the laser diodes (120), wherein the photodiodes (130) are oriented along a second side of the flow chamber (110) opposite the first side such that the laser diodes (120) transmit light directly into the photodiodes (130);

e. a laser control circuitry (140) operatively connected to the laser diodes (120), wherein the laser control circuitry (140) is capable of supplying power to each laser diodes (120) upon receiving a control signal;

f. a signal conditioning circuitry (150) operatively connected to the photodiodes (130), wherein the signal conditioning circuitry (150) amplifies signals from the photodiodes;

g. a housing (160) configured to hold the flow chamber (110), laser diodes (120), and photodiodes (130), the laser control circuitry (140), and the signal conditioning circuitry (150), wherein the housing (160), the plurality of laser diodes (120), and the one or more photodiodes (130) are external to the sample comprising the microalgae culture flowing through the flow chamber (110);

h. a microprocessor (160) operatively connected to the laser control circuitry (140) and the signal conditioning circuitry (150);

i. a memory operatively coupled to the microprocessor (170), the memory stores computer-readable instructions that, when executed by the microprocessor (170), cause the microprocessor (170) to perform operations comprising:
  i. generating the control signal for the laser control circuitry (140), wherein the laser control signal activated at least one of the plurality of laser diodes (120) corresponding to at least one of the plurality of wavelengths of the laser diodes;
  ii. reading at least one voltage signal from the signal conditioning circuitry (150) corresponding to at least one of the photodiodes (130); and
  iii. recording the voltage signals corresponding to the activated wavelengths; and j. a plurality of optical filters disposed in a path of the plurality of laser diodes (120) and the plurality of photodiodes (130), wherein the plurality of optical filters allow only a specific subset of wavelengths produced by the plurality of laser diodes (120) into the plurality of photodiodes (130);

wherein each laser diode (120) emits a focused beam of light into only one photodiode (130); and wherein the plurality of laser diodes (120) and the plurality of photodiodes (130) are disposed outside of the flow chamber (110).

2. The system of claim 1 further comprising a data acquisition system (DAQ) (180) operatively connected to the microprocessor (170), wherein the microprocessor (170) is configured to send the voltage signals and corresponding wavelengths to the DAQ (180), which converts the voltage signals into measurements of one or more biological parameters, wherein the conversion is calibrated to known readings from a second instrument, wherein the DAQ (180) has a graphical user interface that allows a user to monitor measurements in real time.

3. The system of claim 2, wherein the laser control circuitry (140) turns on each laser diode (120) individually via commands received from the DAQ (170).

4. The system of claim 1, wherein the plurality of laser diodes (120) are selected to emit light at wavelengths effective for measuring one or more biological parameters.

5. The system of claim 1, wherein the plurality of laser diodes (120) comprise at least three laser diodes, and wherein the photodiodes (130) comprise at least three photodiodes.

6. The system of claim 5, wherein a first photodiode is configured to detect light from the first laser diode, a second photodiode is configured to detect light from the second laser diode, and a third photodiode is configured to detect light from the third laser diode.

7. The system of claim 1, wherein the plurality of laser diodes (120) are selected to emit light at wavelengths effective for measuring turbidity, cell concentration, and chlorophyll concentrations.

8. The system of claim 7, wherein a first laser diode, a second laser diode, and a third laser diode emit light at center wavelengths of 650, 685, and 780 nm respectively.

9. The system of claim 1, wherein light emitted by the laser diodes (120) is collimated.

10. The system of claim 1, wherein the flow chamber (110) has a light path length effective for providing voltage signal readings that are converted, by the DAQ (180), into measurements of the biological parameters without requiring sample preparation or sample dilution of the microalgae culture.

11. The system of claim 10, wherein the light path length is about 5 mm to 10 mm.

12. The system of claim 1, wherein the photodiodes (130) are disposed on or near the second side (118) of the flow chamber opposite from the laser diodes (120), wherein the photodiodes (130) are oriented to detect light transmitted through the microalgae culture.

13. The system of claim 1, wherein the photodiodes (130) are disposed on or near the flow chamber at an angle with respect to the laser diodes (120), wherein the angle is 0° to less than 180°, wherein the photodiodes (130) are oriented to detect light reflected from the microalgae culture.

* * * * *